Sept. 4, 1962 P. N. ASHLEY Plant Pat. 2,168
WALNUT TREE
Filed Feb. 1, 1960
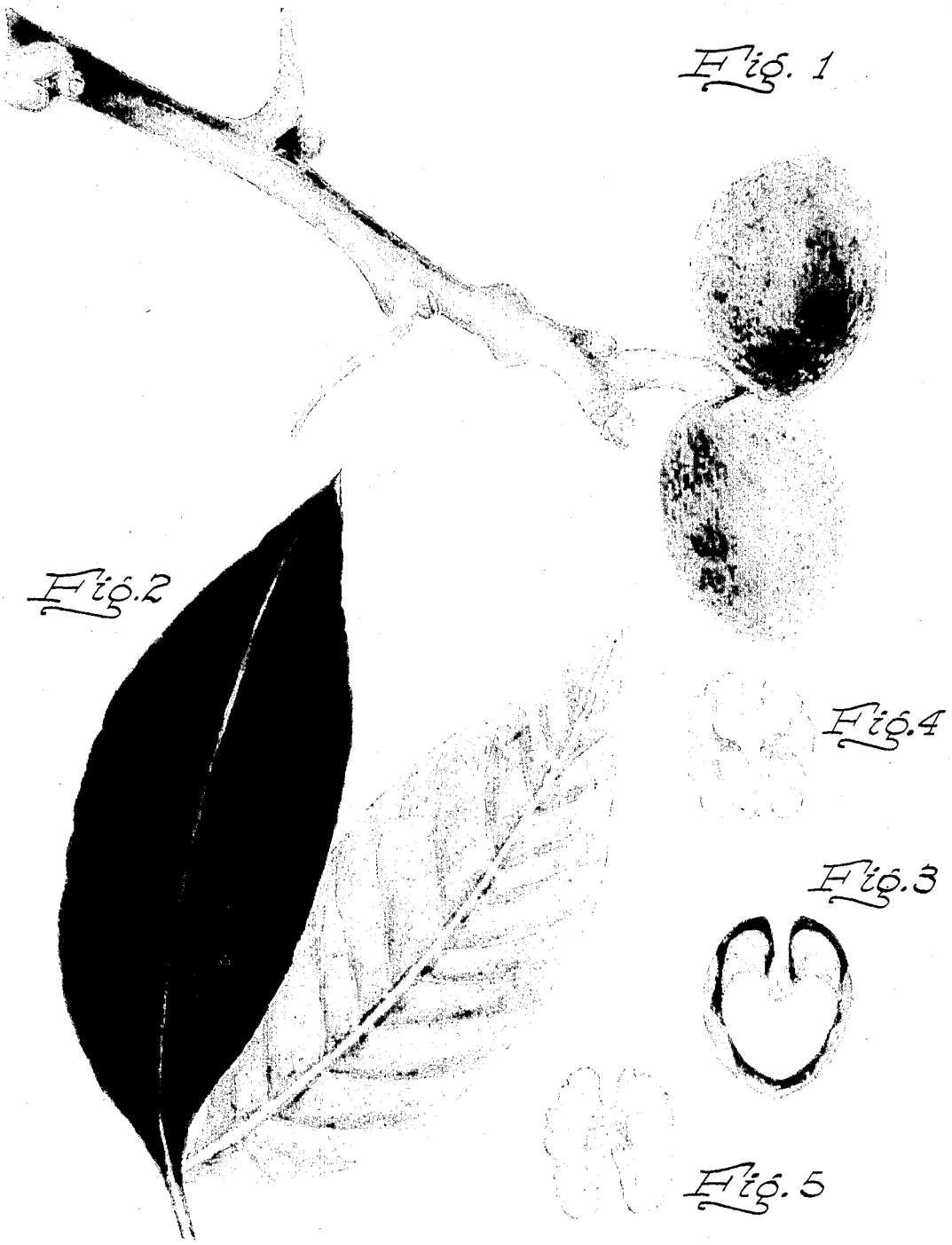
WITNESS
Addison E. Avery
INVENTOR
Pallas Neal Ashley
Webster & Webster
ATTYS.

United States Patent Office

Plant Pat. 2,168
Patented Sept. 4, 1962

2,168
WALNUT TREE

Pallas Neal Ashley, Woodland, Calif., assignor to Stuke Nursery Co., Gridley, Calif., a corporation of California Filed Feb. 1, 1960, Ser. No. 6,085
1 Claim. (Cl. 47—62)

The present discovery relates to a new and distinct variety of English walnut tree generally similar in some respects to the Payne (unpatented), but having certain readily discernible and advantageous features of novelty thereover.

More particularly, the present variety—which has a medium to small size, spreading, much branched, tree with abundant fruiting twigs—is characterized, in comparison to the Payne, by beginning to bear nuts when quite young, i.e. three to four years after budding, and by a heavier yield of commercially acceptable, well filled nuts which are larger, with heavier and smoother, lighter colored, plump kernels which produce a high percentage of crack-out.

A further characteristic of the present variety of walnut tree is that when grown under like conditions of soil and climate it has a leafing time which—while early—is a few days after the Payne, but a few days prior to the Hartley (unpatented).

The present variety was discovered by me in a planting of walnut trees in an orchard located on my ranch near Woodland, California. Such trees, which were budded on conventional black walnut rootstock by a commercial nursery located near Gridley, California, were originally all believed to be of the Hartley variety. However, when such trees came into bearing I recognized the distinctive characteristics of one tree, and which is the variety herein claimed.

The source of the original bud used on such one tree by said commercial nursery is not known to it or to me.

After discovery of the variety, it was asexually reproduced, at my request and on my behalf, by the aforesaid commercial nursery, and such reproductions planted on my ranch, located as aforesaid, ran true to the original tree in all respects. This is also confirmed by asexual reproduction of the variety, with my consent, by the University of California in its experimental orchard at Davis, California.

In the drawings:

FIG. 1 is an elevation of a terminal shoot with nuts and leaf stems.

FIG. 2 illustrates two leaflets in substantially full size; one being shown from the top and the other from the bottom.

FIG. 3 is an elevation of one-half of a shell with the corresponding portion of the kernel remaining therein.

FIG. 4 is an elevation of the kernel removed from the shell.

FIG. 5 is an elevation of a kernel half; the view being taken from the back side.

Referring now more specifically to the botanical details of this new and distinct variety of walnut tree, the following is an outline description thereof; all major color plate identifications being by reference to Maerz and Paul Dictionary of Color, except where common terms of color definition are employed:

Tree:

*Size at maturity.*—Medium to small.
*Growing habit.*—Spreading if unpruned.
*Adaptability.*—Well adapted to the Lower Sacramento and San Joaquin Valleys of California, and other districts where the Payne is now grown.
*Vigor.*—Medium under average growing conditions.
*Wood.*—Trunk—average. Branches—many, spreading, tendency to droop. Fruiting twigs—abundant. Lenticels—prominent. Color of bark—medium.
*Foliage.*—Density—medium. Time of leafing (date when tip buds average 1" in length)—early, a few days after the Payne, but a few days before the Hartley.

Leaves:

*Margin of leaflets.*—Entire.
*Petiole.*—Average.
*Glands.*—None.
*Color of leaflets.*—Top side—medium green (23–L–5). Under side—lighter green (21–L–6).

Flowers:

*Age at which tree starts producing catkins.*—Early.
*Number of catkins produced.*—Average.
*Size of catkins.*—Average.
*Time of pollen shedding.*—Early.
*Age at which tree starts producing pistillate flowers.*—Very early.
*Number of pistillate flowers produced by young trees.*—Very abundant.
*Number of pistillate flowers produced by mature trees.*—Abundant.
*Time when pistillate flowers are receptive.*—Early.
*Coincidence of staminate and pistillate bloom.*—Pollen shed early, but considerable overlap of pistallate bloom.

Nuts:

*Yield.*—Very heavy.
*Quality.*—Very high.
*Evenness of maturity (period between time first and last nuts are ready to harvest).*—Short.
*Time of ripening.*—Early.
*Picking—1958.*—September 16th.
*Picking—1959.*—September 24th.
*Tenacity.*—Average.
*Cluster.*—Average.
*Size.*—Large. Average (in millimeters) of ten nuts from four-year-old tree: Length—1958—44.3; 1959—39.6. Diameter at suture—1958—35.6; 1959—33.8. Diameter cheek to cheek—1958—36.5; 1959—34.9.
*Weight of nuts.*—Average (in grams) of ten nuts from four-year-old tree: 1958—149.2; 1959—114.6.
*Weight of kernels.*—Average (in grams) of ten nuts from four-year-old tree: 1958—81.1; 1959—60.9.
*Percent kernel.*—Average of ten nuts from four-year-old tree: 1958—54.4; 1959—53.1.
*Uniformity of size.*—Average.
*Shape.*—Generally ovoid. Blossom end rounded, symmetrical. Basal end almost flat.
*Color of shell.*—Medium.
*Thickness of shell.*—Thin but tough.
*Seal.*—Fair but adequate.
*Roughness of shell.*—Medium.
*Husk or hull.*—Average. Color—green (18–L–6 to 18–L–7).

Kernel:

*Flavor.*—Good.
*Shape.*—Similar to Payne, but somewhat smoother.
*Texture.*—Good.
*Suture.*—Average.
*Size.*—Large; plump.
*Fill.*—Good.
*Amount of shrivel.*—Sample of ten nuts—none.
*Color.*—Light tan (10–G–4).
*Speckling.*—Lightly to none.
*Veining.*—Lightly to none.

The tree and its nuts herein described may vary in slight detail due to climatic and soil conditions under which this variety may be grown; the present description being of the variety as grown in the Central Valley of California.

The following is claimed:

A new and distinct variety of English walnut tree, as illustrated and described, characterized by a medium to small, spreading, much branched, tree having abundant fruiting twigs; by an early leafing time which, while a few days after the Payne, is a few days before the Hartley; and by an early time of ripening of the nuts; and further characterized—in comparison to the Payne—by beginning to bear nuts when quite young, i.e. three to four years after budding, and by a heavier yield of larger, generally ovoid, thin shelled, well filled, high quality nuts having heavier and smoother, lighter colored, plump kernels.

No references cited.